(12) United States Patent
Morita

(10) Patent No.: US 10,610,199 B2
(45) Date of Patent: Apr. 7, 2020

(54) ACOUSTIC LENS, METHOD FOR PRODUCING SAME, ULTRASOUND PROBE, AND ULTRASOUND IMAGING APPARATUS

(71) Applicant: Konica Minolta, Inc., Tokyo (JP)

(72) Inventor: Kiyokazu Morita, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 977 days.

(21) Appl. No.: 15/152,718

(22) Filed: May 12, 2016

(65) Prior Publication Data

US 2016/0338666 A1 Nov. 24, 2016

(30) Foreign Application Priority Data

May 21, 2015 (JP) ................................ 2015-103576

(51) Int. Cl.
*G10K 11/30* (2006.01)
*A61B 8/00* (2006.01)
*B06B 1/06* (2006.01)

(52) U.S. Cl.
CPC .......... *A61B 8/4281* (2013.01); *A61B 8/4444* (2013.01); *A61B 8/461* (2013.01); *A61B 8/467* (2013.01); *G10K 11/30* (2013.01); *B06B 1/0644* (2013.01)

(58) Field of Classification Search
CPC ......... A61B 8/00; A61B 8/4281; A61B 8/461; A61B 8/467; A61B 8/4444; A61B 5/0075; A61B 1/00009; A61B 1/06; A61B 5/0084; A61B 1/00006; A61B 1/0638; A61B 5/14551; A61B 2576/00; A61B 1/0646; A61B 1/0653; G10K 11/30; B06B 1/0644

See application file for complete search history.

(56) References Cited

U.S. PATENT DOCUMENTS

| | | | |
|---|---|---|---|
| 2005/0070801 A1* | 3/2005 | Yamashita | A61B 8/4281 600/459 |
| 2010/0210745 A1* | 8/2010 | McDaniel | C09D 5/008 521/55 |
| 2011/0240064 A1* | 10/2011 | Wales | C09D 5/14 134/26 |

(Continued)

FOREIGN PATENT DOCUMENTS

| | | |
|---|---|---|
| JP | S62-011897 A | 1/1987 |
| JP | S62-089765 A | 4/1987 |

(Continued)

OTHER PUBLICATIONS

Notice of Reasons for Rejection dated Nov. 6, 2018 from the corresponding Japanese Patent Application No. JP 2015-103576 and English translation.

(Continued)

*Primary Examiner* — Hovhannes Baghdasaryan
*Assistant Examiner* — Amie M Ndure
(74) *Attorney, Agent, or Firm* — Lucas & Mercanti, LLP

(57) ABSTRACT

An acoustic lens contains silicone rubber and metal oxide particles. The metal oxide particles are added into the silicone rubber. The metal oxide particles have a number-average particle diameter of 30 to 2,000 nm, a specific gravity of 3.5 g/cm$^3$ or more, a content of 30 to 150 parts by mass based on 100 parts by mass of the silicone rubber, and an oil absorption amount of 20 mL or less per 100 g.

10 Claims, 2 Drawing Sheets

(56) References Cited

U.S. PATENT DOCUMENTS

| | | | | |
|---|---|---|---|---|
| 2011/0250626 A1* | 10/2011 | Williams | ............... | A01N 63/02 435/18 |
| 2012/0097194 A1* | 4/2012 | McDaniel | .............. | A01N 63/02 134/26 |
| 2013/0011617 A1 | 1/2013 | Tasaki et al. | | |

FOREIGN PATENT DOCUMENTS

| | | |
|---|---|---|
| JP | 2003-012787 A | 1/2003 |
| JP | 2009072605 A | 4/2009 |
| JP | 2011072702 A | 4/2011 |
| JP | 2013-188465 A | 9/2013 |
| WO | 2011/118108 A1 | 9/2011 |

OTHER PUBLICATIONS

Official Notice of Reasons for Rejection dated Mar. 12, 2019 from the corresponding Japanese Patent Application No. JP 2015-103576 and English translation.

* cited by examiner

ACOUSTIC LENS, METHOD FOR PRODUCING SAME, ULTRASOUND PROBE, AND ULTRASOUND IMAGING APPARATUS

CROSS REFERENCE TO RELATED APPLICATIONS

This application is entitled to and claims the benefit of Japanese Patent Application No. 2015-103576, filed on May 21, 2015, the disclosure of which including the specification, drawings and abstract is incorporated herein by reference in its entirety.

BACKGROUND OF THE INVENTION

1. Field of the Invention

The present invention relates to an acoustic lens, a method for producing the same, an ultrasound probe having the acoustic lens, and an ultrasound imaging apparatus.

2. Description of Related Art

Ultrasound imaging apparatuses which use ultrasound for testing transmit ultrasound to a test subject (e.g., living organism) and receive a reflection wave (echo) of this ultrasound to thereby visualize the inside of the test subject for testing.

In an ultrasound imaging apparatus, an acoustic lens for an ultrasound probe is used in close contact with a test subject, and thus is required to have properties as mentioned below. From the viewpoint of suppressing the reflection (multiple reflection) of ultrasound between the acoustic lens and the test subject, the acoustic impedance of the acoustic lens is required to be close to that of the test subject. Further, from the viewpoint of high sensitivity, the attenuation factor of sound in the acoustic lens is required to be low. Furthermore, from the viewpoint of adaptation to various shapes of the acoustic lens, the moldability of the acoustic lens is required to be high. Thus, acoustic lenses for satisfying these requirements have been proposed (e.g., Japanese Patent Application Laid-Open No. 2011-072702 and Japanese Patent Application Laid-Open No. 2009-072605).

The acoustic lens disclosed in Japanese Patent Application Laid-Open No. 2011-072702 contains silicone rubber and metal oxide particles coated with silica. In this acoustic lens, the use of fine metal oxide particles having an average particle diameter of 30 nm may reduce the attenuation factor of sound.

The acoustic lens disclosed in Japanese Patent Application Laid-Open No. 2009-072605 contains silicone rubber and metal oxide particles. In this acoustic lens, the use of high-density zinc oxide, platinum oxide or ytterbium oxide as metal oxide particles may reduce the attenuation factor of sound.

In the acoustic lens disclosed in Japanese Patent Application Laid-Open No. 2011-072702, however, 10 to 60 parts by mass of metal oxide particles are required when the acoustic impedance is tried to be close to that of the test subject. Further, in the acoustic lens disclosed in Japanese Patent Application Laid-Open No. 2009-072605, 15 to 60 parts by mass of zinc oxide, 10 to 52 parts by mass of platinum oxide, or 12 to 56 parts by mass of ytterbium oxide is required, when the acoustic impedance is tried to be close to that of the test subject. Thus, in the acoustic lenses disclosed in the above-mentioned patent literatures, it is required to mix large amounts of metal oxide particles in order to obtain desired acoustic properties. However, when large amounts of metal oxide particles are mixed into silicone rubber, the metal oxide particles cannot be mixed into silicone rubber uniformly and stably. That is, the mixing property between metal oxide particles and silicone rubber becomes low. When the mixing property between metal oxide particles and silicone rubber thus becomes low, there is a concern that streak-shaped crystal defect (hereinafter, also referred to as "failure") may undesirably occur in forming the acoustic lens. Accordingly the acoustic lenses disclosed in the above-mentioned patent literatures have room for improvement with regard to the mixing property between metal oxide particles and silicone rubber.

SUMMARY OF THE INVENTION

A first object of the present invention is to provide an acoustic lens having excellent acoustic properties and being excellent in mixing property between metal oxide particles and silicone rubber. In addition, a second object of the present invention is to provide an ultrasound probe and an ultrasound imaging apparatus having the acoustic lens.

In order to achieve the first object, the acoustic lens that reflects one aspect of the present invention is an acoustic lens for an ultrasound probe, and is composed of a vulcanized molded rubber composition containing silicone rubber and metal oxide particles dispersed in the silicone rubber, in which the metal oxide particles have a number-average particle diameter of 30 to 2,000 nm, a specific gravity of 3.5 g/cm$^3$ or more, a content of 30 to 150 parts by mass based on 100 parts by mass of the silicone rubber, and an oil absorption amount of 20 mL or less per 100 g.

In order to achieve the first object, the method for producing the acoustic lens that reflects one aspect of the present invention is a method for producing an acoustic lens for an ultrasound probe, the method including: producing a rubber composition by kneading silicone rubber with metal oxide particles; and vulcanizing and molding the rubber composition, in which the metal oxide particles having a number-average particle diameter of 30 to 2,000 nm, a specific gravity of 3.5 g/cm$^3$ or more, a content of 30 to 150 parts by mass based on 100 parts by mass of the silicone rubber, and an oil absorption amount of 20 mL or less per 100 g are used.

In order to achieve the second object, the ultrasound probe that reflects one aspect of the present invention has the acoustic lens that reflects one aspect of the present invention.

In order to achieve the second object, the ultrasound imaging apparatus that reflects one aspect of the present invention has the ultrasound probe that reflects one aspect of the present invention.

BRIEF DESCRIPTION OF DRAWINGS

The present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Figure 1:
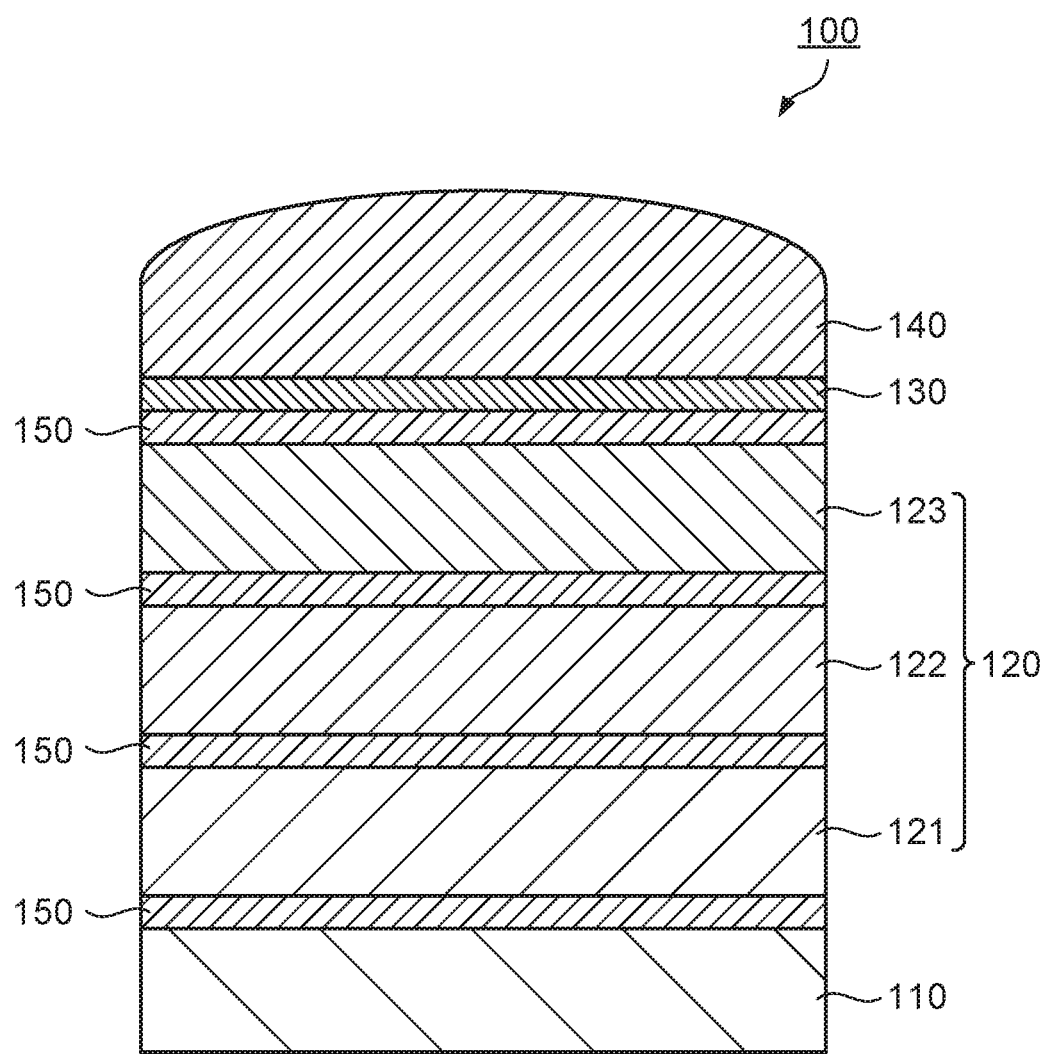
FIG. 1 is a cross-sectional schematic diagram illustrating a configuration of an ultrasound probe according to an embodiment of the present invention.

The ultrasound probe according to an embodiment of the present invention will be described in detail with reference to the attached drawings. FIG. 1 is a cross-sectional schematic diagram illustrating a configuration of the ultrasound probe according to the present embodiment.

Ultrasound probe 100 of the present embodiment includes backing layer 110, piezoelectric element 120 disposed on backing layer 110, acoustic matching layer 130 disposed on piezoelectric element 120, and acoustic lens 140 according to the present embodiment disposed on acoustic matching layer 130. Piezoelectric element 120 has transmitting piezoelectric 121 disposed on backing layer 110, intermediate layer 122 disposed on transmitting piezoelectric 121, and receiving piezoelectric 123 disposed on intermediate layer 122. Further, electrodes 150 are each disposed on both surfaces of transmitting piezoelectric 121 and receiving piezoelectric 123.

[Backing Layer]

Backing layer 110 is an ultrasound absorber which supports piezoelectric element 120 and which may absorb unnecessary ultrasound.

Examples of the material for backing layer 110 include natural rubber, ferrite rubber, an epoxy resin, a thermoplastic resin, and a resin-based composite material obtained by press-molding a mixture of at least one of these materials and powder such as tungsten oxide, titanium oxide, or ferrite.

Examples of the thermoplastic resin include vinyl chloride, polyvinyl butyral, ABS resin, polyurethane, polyvinyl alcohol, polyethylene, polypropylene, polyacetal, polyethylene terephthalate, fluorine resin, polyethylene glycol, and polyethylene terephthalate-polyethylene glycol copolymer. As the material for backing layer 110, a resin-based composite material is preferred, and a rubber-based composite material or epoxy resin-based composite material is particularly preferred. The shape of backing layer 110 may be appropriately designed depending on the shape of piezoelectric element 120 or the shape of ultrasound probe 100 including piezoelectric element 120.

The rubber-based composite material preferably contains a rubber component and a filler, which are described later. Further, other compounding agents may be added to the rubber-based composite material, as necessary.

Examples of the rubber component include ethylene propylene rubber, hydrogenated nitrile rubber, chloroprene rubber, silicone rubber, blended rubber of ethylene propylene rubber and hydrogenated nitrile rubber, blended rubber of ethylene propylene rubber and nitrile rubber, blended rubber of nitrile rubber and/or hydrogenated nitrile rubber and high styrene rubber, and blended rubber of ethylene propylene rubber and high styrene rubber. Either one type of rubber component or two or more types thereof may be employed. It is preferable that the hardness of the rubber component as measured using a spring hardness (durometer hardness) tester in accordance with HS K 6253 is A70 or more when a type A durometer is used, and is D70 or less when a type D durometer is used.

The type and the compounding amount of the filler to be added to the rubber-based composite material are not particularly limited. Examples of the filler include metal oxides such as zinc white, titanium white, red iron oxide, ferrite, alumina, tungsten trioxide, and ytterbium oxide; clays such as calcium carbonate, hard clay, and diatomaceous earth; metal salts such as calcium carbonate and barium sulfate; metal fine powders such as tungsten and molybdenum; balloons such as glass balloon and polymer balloon; and glass powder. These additives may be added at various ratios, and are within a range of preferably 50 to 3,000 parts by mass, more preferably 100 to 2,000 parts by mass, and even more preferably 300 to 1,500 parts by mass, based on 100 parts by mass of the rubber component. Either one type of filler or two or more types thereof may be employed.

Examples of other compounding agents include a vulcanizing agent, a cross-linking agent, a curing agent, an auxiliary agent therefor, an antidegradant, an antioxidant, and a colorant. Examples of the vulcanizing agent include carbon black, silicon dioxide, process oil, and sulfur. Examples of the cross-linking agent include dicumyl peroxide (DI-CUP; "DI-CUP" is a registered trademark of Hercules, Inc.). Examples of the antioxidant include stearic acid. The addition amount of the compounding agent may be appropriately set depending on the properties of an acoustic lens. The addition amount of each compounding agent is, for example, within a range of 1 to 100 parts by mass based on 100 parts by mass of a rubber component.

The epoxy resin-based composite material preferably contains an epoxy resin component and a filler, which are described later. In addition, other compounding agents may be added to the epoxy resin composite material, as necessary.

Examples of the epoxy resin component include novolac-type epoxy resins such as bisphenol A, bisphenol F type, resol novolac type, and phenol-modified novolac type; polycyclic aromatic epoxy resins such as naphthalene structure-containing type or anthracene structure-containing type, and fluorene structure-containing type; hydrogenated alicyclic epoxy resins; and liquid crystal epoxy resins. Either one type of epoxy resin component or two or more types thereof may be employed.

Examples of the filler to be added to the epoxy resin-based composite material are similar to the filler to be added to the rubber-based composite material mentioned above. Further, the epoxy resin component may contain composite particles (having a particle diameter of, e.g., about 200 μm) produced by pulverization of the rubber-based composite material. For example, the composite particles are particles produced by pulverizing silicone rubber with ferrite being added thereto using a pulverizer.

When the epoxy resin composite material is used, it is necessary to further add a cross-linking agent. Examples of the cross-linking agent include chain aliphatic polyamines such as diethylenetriamine, triethylenetetramine, dipropylenediamine, and diethylaminopropylamine; cyclic aliphatic polyamines such as N-aminoethylpiperazine, menthanediamine, and isophoronediamine; aromatic amines such as m-xylenediamine, metaphenylenediamine, diaminodiphenylmethane, and diaminodiphenylsulfone; secondary or tertiary amines such as polyamide resin, piperidine, N,N-dimethylpiperazine, triethylenediamine, 2,4,6-tris(dimethylaminomethyl)phenol, benzyldimethylamine, and 2-(dimethylaminomethyl)phenol; imidazols such as 2-methylimidazol, 2-ethylimidazol, 1-cyanoethyl-2-undecylimidazolium.trimellitate; and acid anhydrides such as liquid polymercaptan, polysulfide, phthalic anhydride, trimellitic anhydride, methyl tetrahydrophthalic anhydride, methyl endo-methylenetetrahydrophthalic anhydride, methyl butenyltetrahydrophthalic anhydride, and methyl hexahydrophthalic acid.

The thickness of backing layer 110 is within a range of preferably 1 to 10 mm, and more preferably 1 to 5 mm.

[Piezoelectric Element]

Piezoelectric element 120 can convert electric signals into a mechanical oscillation, and also converts a mechanical oscillation into electric signals. Thus, piezoelectric element 120 can transmit and receive ultrasound. From the viewpoint of enhancing the adhesion between piezoelectric element 120 and backing layer 110, at least a part of piezoelectric element 120 is preferably layered on backing layer 110 with an adhesive layer being disposed therebetween. As the material for the adhesive layer, it is sufficient to use, for example, a silicone-based adhesive or an epoxy-based adhesive.

As described above, piezoelectric element 120 includes transmitting piezoelectric 121, intermediate layer 122 and receiving piezoelectric 123. Electrodes 150 are each disposed on both surfaces of transmitting piezoelectric 121 and receiving piezoelectric 123.

Transmitting piezoelectric 121 is a piezoelectric used for transmitting ultrasound toward a test subject. Receiving piezoelectric 123 is a piezoelectric used for receiving ultrasound from the test subject. The piezoelectric used for each of transmitting piezoelectric 121 and receiving piezoelectric 123 is a piezoelectric known substance, mixture, compound, solid solution or composition, or may be either an inorganic substance or an organic substance.

Examples of the material for the inorganic piezoelectric include crystal, lithium niobate, barium titanate, lead titanate, lead metaniobate, zinc oxide, $PbZrO_3/PbTiO_3$ solid solution (PZT), $Pb(Mg_{1/3}Nb_{2/3})O_3/PbTiO_3$ solid solution (PMN-PT), and $Pb(Zn_{1/3}Nb_{2/3})O_3/PbTiO_3$ solid solution (PZN-PT).

Examples of the material for the organic piezoelectric include electrets of vinylidene polyfluoride-ethylene trifluoride copolymer (P(VDF-3FE)), a kneaded mixture of (P(VDF-3FE) and a polyurethane, a kneaded mixture of (P(VDF-3FE) and a silicone, a kneaded mixture of vinylidene polyfluoride and nylon, a PVDF-based copolymer obtained by copolymerization of vinylidene fluoride and chlorotrifluoroethylene, polybutadiene-N,N-methylenebisacrylamide-styrene copolymer, poly(γ-benzyl-L-glutamate), a polyurea resin obtained by vapor deposition polyaddition between methanediisocyanate and diaminofluorene, a polyurea resin obtained by vapor deposition polyaddition between xylylenediisocyanate and p-diaminobenzene, and tetrafluoroethylene-hexafluoropropylene copolymer.

Further, examples of the material for an inorganic-organic composite piezoelectric include a PZT-siloxane-poly(meth) acrylate composite, and a composite of polylactic acid and calcium phosphate or montmorillonite.

The thickness of each of transmitting piezoelectric 121 and receiving piezoelectric 123 is not particularly limited as long as they can perform the above-mentioned functions, and is, for example, within a range of 100 to 500 μm.

Intermediate layer 122 is disposed between transmitting piezoelectric 121 and receiving piezoelectric 123 from the viewpoint of impedance matching. Intermediate layer 122 is, for example, a layer obtained by mixing 1,200 parts by mass of ferrite with 100 parts by mass of an epoxy resin.

Electrodes 150 are each disposed on both surfaces of transmitting piezoelectric 121 and receiving piezoelectric 123. Electrode 150 may be formed either on the entire surface of transmitting piezoelectric 121 and receiving piezoelectric 123, or on a part of the surface thereof. Examples of the material for electrode 150 include gold, platinum, silver, palladium, copper, aluminum, nickel, tin, and an alloy thereof. The method for forming electrode 150 on both surfaces of transmitting piezoelectric 121 and receiving piezoelectric 123 is not particularly limited. For example, in order to form electrode 150, an underlying metal such as titanium or chromium may be formed to have a thickness of 0.02 to 1.0 μm by sputtering method or vapor deposition method, and then the electrode 150 may be formed to have a thickness of 1 to 10 μm by sputtering method or vapor deposition method. In addition, electrode 150 may also be formed by screen printing, a dipping method, or thermal spraying method using a conductive paste in which fine metal powder and low-melting point glass are mixed.

[Acoustic Matching Layer]

Acoustic matching layer 130 is a layer for matching acoustic impedance between piezoelectric element 120 and a test subject. For this purpose, acoustic matching layer 130 has acoustic impedance of intermediate magnitude between piezoelectric element 120 and a test subject. Acoustic matching layer 130 may be either a single layer or layered, and is preferably a layered product composed of a plurality of layers having different acoustic impedances. For example, acoustic matching layer 130 is composed of preferably two layers or more, and more preferably four layers or more. The thickness of acoustic matching layer 130 is λ/4, when the wavelength of ultrasound is set as 2. When this value of thickness is not satisfied, there is a concern that desired acoustic properties may not be achieved.

Acoustic matching layer 130 can be composed of various materials, for example. The acoustic impedance of acoustic matching layer 130 is preferably set so as to be closer to the acoustic impedance of acoustic lens 140 stepwise or continuously toward acoustic lens 140. For example, the acoustic impedance of acoustic matching layer 130 may be adjusted by the type of an additive to be added to the material and the content of the additive.

Examples of the material for acoustic matching layer 130 include aluminum, an aluminum alloy (e.g., Al—Mg alloy), a magnesium alloy, Macor glass, glass, fused quartz, copper graphite, and resin. Examples of the resin include polyethylene, polypropylene, polycarbonate, ABS resin, AAS resin, AES resin, nylon such as nylon 6, nylon 66, polyphenylene oxide, polyphenylene sulfide, polyphenylene ether, polyetheretherketone, polyamideimide, polyethylene terephthalate, epoxy resin, and urethane resin. Examples of the additive include zinc white, titanium oxide, silica, alumina, red iron oxide, ferrite, tungsten oxide, ytterbium oxide, barium sulfate, tungsten, molybdenum, glass fiber, and silicone particles.

From the viewpoint of impedance matching of acoustic matching layer 130, it is preferable, for example, that the surface part of acoustic matching layer 130 is composed of an epoxy resin and contains silicone particles. By dispersing a silicone which is a material for acoustic lens 140 in the base material of acoustic matching layer 130, it becomes possible to allow the acoustic impedance of acoustic matching layer 130 to be close to that of acoustic lens 140.

The thickness of acoustic matching layer 130 is not particularly limited as long as it can perform the above-mentioned functions, and is, for example, within a range of 30 to 500 μm.

From the viewpoint of enhancing the adhesion between piezoelectric element 120 and acoustic matching layer 130, at least a part of acoustic matching layer 130 is preferably layered on piezoelectric element 120 with an adhesive layer being disposed therebetween. As the material for the adhesive layer, it is sufficient to use, for example, a silicone-based adhesive or an epoxy-based adhesive.

[Acoustic Lens]

Acoustic lens 140 according to the present embodiment is composed of a vulcanized molded rubber composition containing silicone rubber and metal oxide particles dispersed in the silicone rubber.

(Silicone Rubber)

The silicone rubber is a rubber-like silicone resin having siloxane bonds (Si—O bond) as a molecular skeleton. The rubber-like silicone resin having dimethylpolysiloxane as a main component is preferred. The polymerization degree of the rubber-like silicone resin is, for example, within a range of preferably 3,000 to 10,000. From the viewpoints of adjustments of sound velocity and density of acoustic lens 140, an organic or inorganic filler such as silica or nylon powder may be contained. It is preferable that a silicone compound represented by the following formula (1) is further contained. In the following formula (1), the order of $R^1_2SiO$ portion and $R^1R^2SiO$ portion may be either continuous or random.

$$R^1(R^1_2SiO)_X(R^1R^2SiO)_Y Si\ R^1_3 \qquad (1)$$

(where $R^1$ is a monovalent hydrocarbon group or a hydrogen atom, $R^2$ is an alkyl group or polyether group, X is an integer of 0 or more, and Y is an integer of 1 or more)

The silicone rubber can be obtained as a commercially available product. Examples of the silicone rubber that can be used include KE520U, KE541U, KE742U, KE752U, KE922U, KE931U, KE941U, KE951U, KE961U, KE850U, KE555U, and KE575U manufactured by Shin-Etsu Chemical Co., Ltd.; TSE200A, TSE201, TSE221-3U, TE221-4U, TSE2233U, XE20-523-4U, TSE27-4U, TSE260-3U, and TSE-260-4U manufactured by Momentive Performance Materials Inc.; and SH35U, SH55UA, SH745, SH746, SH831U, SE6749U, SE1120U, and SE4704U manufactured by Toray Dow Corning Corporation.

(Metal Oxide Particles)

The metal oxide particles are dispersed in the silicone rubber. The oil absorption amount per 100 g of the metal oxide particles is 20 mL or less, and preferably 15 mL or less. When the oil absorption amount is more than 20 mL, the mixing property between the metal oxide particles and the silicone rubber is lowered, so that acoustic lens 140 cannot be manufactured stably. In addition, the lowering of the mixing property causes the attenuation factor of sound in acoustic lens 140 to be increased, so that it becomes not possible to obtain desired acoustic impedance. The oil absorption amount may be either a measurement value or a catalogue value. The oil absorption amount may be measured by means of refined linseed oil method (JIS K 5101-13-1) or boiled linseed oil method (JIS K 5101-13-2). Note that the oil absorption amount of metal oxide particles added into the silicone rubber of molded acoustic lens 140 can be estimated from the particle diameter and the porosity of the metal oxide particles.

Generally, the oil absorption amount depends on the particle diameter and the porosity of metal oxide particles. As the particle diameter of the metal oxide particles becomes larger, the oil absorption amount becomes smaller. Further, as the porosity of the metal oxide particles becomes smaller, the percentage of the surface area per unit volume becomes smaller, causing the oil absorption amount to be smaller. In particular, the oil absorption amount is largely affected by the porosity of metal oxide particles. The particle diameter and the porosity of the metal oxide particles according to the present embodiment are adjusted such that the oil absorption amount per 100 g of the metal oxide particles is 20 mL or less.

The metal oxide particles may support a support material on the surface thereof. Examples of the support material include aluminum oxide (isoelectric point: pH 9.1 to 9.5), silica (isoelectric point: pH 1.5 to 3.5), zirconium oxide (isoelectric point: pH 6.0 to 7.0), and a combination thereof.

Further, other substances may be added to the support material, as necessary. For example, from the viewpoint of stabilization, a small amount (about 3 mol %) of yttrium oxide ($Y_2O_3$) may be added to zirconium oxide. At that time, the isoelectric point of zirconium oxide to which $Y_2O_3$ is added is about pH 10. Further, the surface of the metal oxide particles is preferably basic. Thus, it becomes possible to allow the silicone rubber having acidic properties and the metal oxide particles to easily interact with each other, further enhancing the mixing property between the metal oxide particles and the silicone rubber. From such a point of view, the support material is preferably aluminum oxide or zirconium oxide, and more preferably aluminum oxide. The method for supporting the support material on the surface of the metal oxide particles is not particularly limited, and may be appropriately selected from known methods depending on a desired surface shape and the degree of basicity.

The metal oxide particles on which a support material is supported on the surface thereof may be prepared by bringing the metal oxide particles into contact with a mixed solution containing a coating agent, water, an alkali and an organic solvent. Thus, a support material is selectively deposited on the surface of the metal oxide particles. The coating agent contains a support material such as an aluminum coupling agent, silicic acid, a silane coupling agent, and a zirconia coupling agent. At that time, from the viewpoint of selectively depositing a support material on the surface of the metal oxide particles, water/organic solvent ratio is within a range of 0.1 to 10 in terms of volume ratio, and the concentration of the support material is preferably within a range of 0.0001 to 5 mol/L.

An example of the method for supporting the support material on the surface of the metal oxide particles will be described. First, rutile type titanium oxide ($TiO_2$) particles as metal oxide particles are prepared into aqueous slurry having a $TiO_2$ concentration of 200 g/dm³. Then, to this aqueous slurry is added 0.4 parts by mass of hexametaphosphate ($Na_nH_2PnO_{3n+1}$) as $P_2O_5$ based on titanium oxide, followed by wet grinding using a bead mill, and coarse particles are separated using a 200 mesh. The concentration of the slurry after the coarse particles are separated is adjusted to 200 g/dm³, and the temperature of the slurry is raised to 70° C. While keeping the temperature of the slurry elevated, 3 parts by mass of an aqueous sodium silicate solution in terms of $SiO_2$ based on $TiO_2$ is added over 30 minutes, and then the temperature is raised to 85° C. After the slurry is stirred for 30 minutes, dilute sulfuric acid is slowly added dropwise over 40 minutes to neutralize the slurry to pH 7.0. The neutralized slurry is cooled to 70° C. and the pH thereof is adjusted to 5.5 with dilute sulfuric acid, and subsequently 1 part by mass of an aqueous sodium aluminate solution in terms of $Al_2O_3$ based on $TiO_2$ is added over 30 minutes. After the slurry is stirred for 30 minutes, the pH of the slurry is readjusted to 5.5 with dilute sulfuric acid, followed by filtering and washing. Finally, the filtered solid content is dried at 120° C., and pulverized with air flow. Thus, titanium oxide particles on which aluminum oxide is supported on the surface thereof can be prepared.

The film thickness of the support material is within a range of preferably 0.1 to 100 nm, and more preferably 1 to 25 nm.

The number-average particle diameter of the metal oxide particles is within a range of 30 to 2,000 nm, preferably 50 to 1,000 nm, and more preferably 100 to 500 nm. When the number-average particle diameter of the metal oxide particles is more than 2,000 nm, the metal oxide particles scatter ultrasound, causing the attenuation factor of acoustic lens 150 to be decreased. When the number-average particle diameter of the metal oxide particles is less than 30 nm, the mixing property of the metal oxide particles into silicone rubber is undesirably lowered. The number-average particle diameter of the metal oxide particles is a number-average value of measured values of particle diameters of 100 particles by means of electron microscope observation. As used herein, the particle diameter is an average value of the major axis and the minor axis of a particle determined by an image by electron microscope observation. Note that the number-average particle diameter may be either a measurement value or a catalogue value.

The content of the metal oxide particles is, for example, within a range of 30 to 150 parts by mass (3 to 29 parts by volume) based on 100 parts by mass of silicone rubber. When the content of the metal oxide particles is less than 30 parts by mass, it is not possible to obtain desired acoustic impedance. Further, the content of the metal oxide particles is more than 150 parts by mass, the mixing property between the metal oxide particles and the silicone rubber is undesirably lowered.

The specific gravity of the metal oxide particles is, for example, 3.5 g/cm$^3$ or more, and preferably 4.0 g/cm$^3$ or more. When the specific gravity of the metal oxide particles is less than 3.5 g/cm$^3$, it is required to add large amounts of the metal oxide particles into the silicone rubber, causing the mixing property between the metal oxide particles and the silicone rubber to be lowered. Note that the specific gravity of the metal oxide particles may be either a measurement value or a catalogue value.

The metal oxide in the metal oxide particles is not particularly limited. Example of the metal oxide include $TiO_2$, $SnO_2$, $Bi_2O_3$, $WO_3$, $ZrO_2$, $Fe_2O_3$, $MnO_2$, $Y_2O_3$, MgO, $Fe_2O_3$, $BaSO_4$, $CaCO_3$, and a combination thereof. Note that rutile type $TiO_2$ is preferred as $TiO_2$.

The metal oxide particles can be obtained as a commercially available product. Examples of titanium oxide particles that can be used include CR-50, CR-50-2, CR-57, CR-58, CR-58-2, CR-60, CR-60-2, CR-63, CR-67, CR-Super70, CR-80, CR-90-2, CR-93, CR-95, CR-953, CR-97, PF-690, PF-691, PF-711, PF-736, PF-737, PF-739, PF-740, PC-3, UT771, R-580, R-630, R-680, R-930, R-980 and TTO-55(C) manufactured by Ishihara Sangyo Kaisha, Ltd.; and R-62N, GTR-100, R-39, and R-11.P manufactured by Sakai Chemical Industry Co., Ltd. Further, as barium sulfate particles, it is possible to use B-30, B-32, B-33, B-34, and BF-10 manufactured by Sakai Chemical Industry Co., Ltd.

Here, an example of the method for producing acoustic lens 140 will be described. First, acoustic lens 140 is produced by the steps of producing a rubber composition by kneading silicone rubber with metal oxide particles, and vulcanizing and molding the rubber composition.

Secondary vulcanization may also be performed as necessary, and a vulcanization aid such as sulfur or zinc oxide may be further added. The use of zinc oxide as a vulcanization aid facilitates vulcanization without substantially impairing the lens properties of acoustic lens 140 to shorten the vulcanizing time. Further, other additives such as silica powder, titanium oxide, alumina, cerium oxide, iron oxide, barium sulfate, an organic filler, and a coloring pigment may also be added within such a range as not to impair the properties of acoustic lens 140. At that time, the content of silica powder is preferably within a range of 20 parts by mass or less, and the content of other additives is preferably within a range of 5 parts by mass or less.

Examples of the vulcanizing agent include peroxide-based vulcanizing agents such as 2,5-dimethyl-2,5-ditertiary butylperoxy hexane, p-methyl benzoyl peroxide, and ditertiary butyl peroxide. The addition amount of the vulcanizing agent is, for example, within a range of preferably 0.3 to 5 parts by mass based on 100 parts by mass of the silicone rubber.

When mixing the silicone rubber with the metal oxide particles, it is preferable to remove moisture attached to the metal oxide particles by heating or the like. Further, the temperature for vulcanizing and molding is preferably within a range of 100 to 200° C.

Ultrasound probe 100 according to the present embodiment has acoustic lens 140 containing metal oxide particles having an oil absorption amount of 20 mL or less per 100 g. Thus, it is deduced that a low-molecular-weight component in the silicone rubber presumed to contribute to the mixing property of the metal oxide particles into the silicone rubber effectively forms a protective layer on the surface of the metal oxide particles. It is deduced that the protective layer enables the metal oxide particles to be easily dispersed in the silicone rubber to suppress the occurrence of failure at the time when molding acoustic lens 140. Accordingly, ultrasound probe 100 and acoustic lens 140 according to the present embodiment may be produced stably in high yield.

While the description is made for ultrasound probe 100 according to the present embodiment in the case of using piezoelectric element 120 having transmitting piezoelectric 121 and receiving piezoelectric 123, it is also possible to employ a single piezoelectric which performs both the transmission and reception of ultrasound.

While the description is made for ultrasound probe 100 according to the present embodiment in the case of disposing transmitting piezoelectric 121 and receiving piezoelectric 123 vertically, it is also possible to dispose transmitting piezoelectric 121 and receiving piezoelectric 123 in parallel.

Figure 2A:
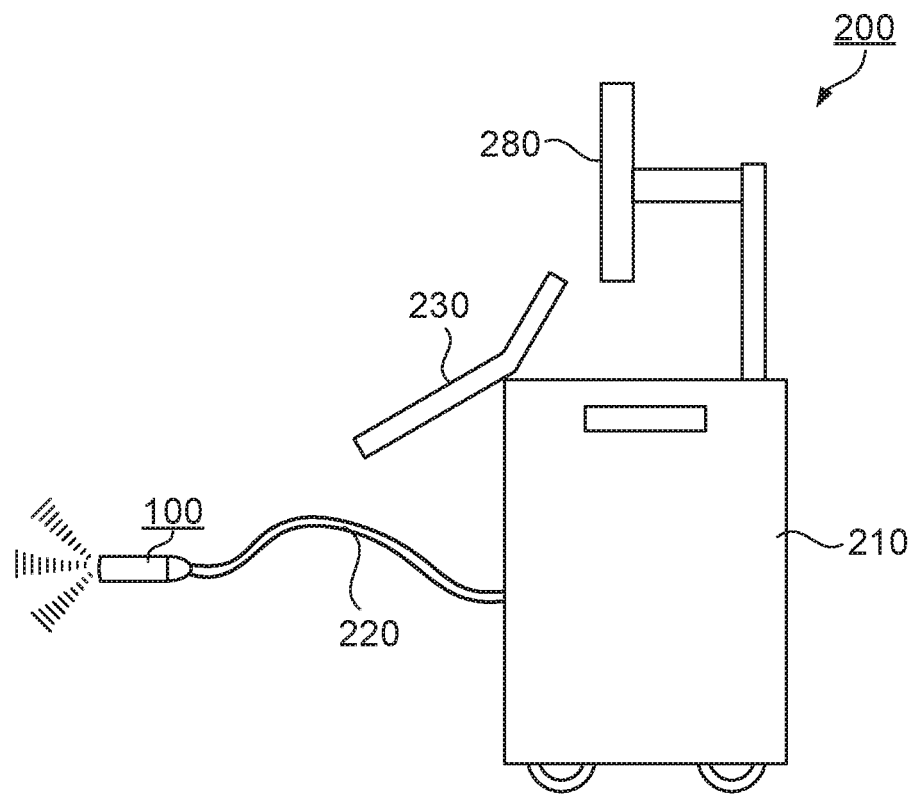
FIG. 2A is schematic diagram illustrating a configuration of an ultrasound imaging apparatus according to an embodiment of the present invention.

Next, the ultrasound imaging apparatus according to the present embodiment will be described. FIG. 2A is schematic diagram illustrating a configuration of ultrasound imaging apparatus 200 according to the present embodiment, and FIG. 2B is a block diagram illustrating an electrical configuration of ultrasound imaging apparatus 200.

As illustrated in FIG. 2A, ultrasound imaging apparatus 200 includes apparatus body 210, ultrasound probe 100 connected to apparatus body 210 via cable 220, input section 230 disposed on apparatus body 120, and display section 280.

Figure 2B:
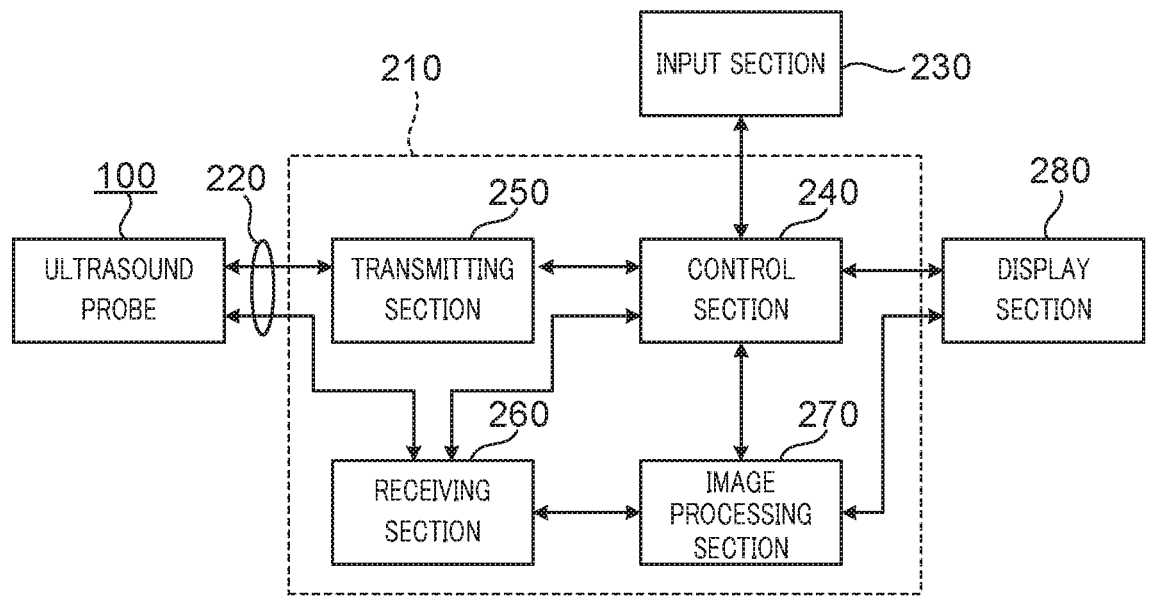
FIG. 2B is a block diagram illustrating an electrical configuration of the ultrasound imaging apparatus.

As illustrated in FIG. 2B, apparatus body 210 includes control section 240 connected to input section 230, transmitting section 250 and receiving section 260 which are connected to both control section 240 and cable 220, and image processing section 270 connected to each of receiving section 260 and control section 240. Note that each of control section 240 and image processing section 270 is connected to display section 280.

Cable 220 connects ultrasound probe 100 to each of transmitting section 250 and receiving section 260 to communicate signals.

Input section 230 is, for example, a device for inputting a command to give a direction such as starting diagnosis or data such as individual information of a test subject, and is, for example, an operation panel provided with a plurality of input switches or a keyboard.

Control section 240 includes, for example, a microprocessor, a storage element, a peripheral circuit thereof, and the like. Control section 240 is a circuit that controls ultrasound probe 100, input section 230, transmitting section 250, receiving section 260, image processing section 270 and display section 280 depending on their functions to thereby control entire ultrasound imaging apparatus 200.

Transmitting section 250, for example, transmits signals from control section 240 to ultrasound probe 100 via cable 220.

Receiving section 260, for example, receives signals from ultrasound probe 100 via cable 220 to output them to control section 240 or image processing section 270.

Image processing section 270 is, for example, a circuit that forms an image (ultrasound image) representing the internal state of a test subject based on signals received at receiving section 260 under the control of control section 240. For example, image processing section 270 includes a digital signal processor (DSP) that generates an ultrasound image of a test subject, and a digital-analog conversion circuit (DAC circuit) that converts signals processed at the DSP from digital signals to analog signals.

Display section 280 is a device for displaying the ultrasound image of the test subject generated at image processing section 270 under the control of control section 240. Display section 280 is, for example, a display apparatus such as a CRT display, liquid crystal display (LCD), organic EL display or plasma display, or a printing apparatus such as a printer.

Ultrasound probe 100 in ultrasound imaging apparatus 200 according to the present embodiment includes acoustic lens 140 containing metal oxide particles having an oil absorption amount of 20 mL or less. Ultrasound imaging apparatus 200 includes ultrasound probe 100 (acoustic lens 140) excellent in acoustic properties, and thus can test a test subject with high accuracy and reliability.

Ultrasound imaging apparatus 200 is applicable to medical ultrasound diagnostic equipment. Further, ultrasound imaging apparatus 200 is also applicable to other apparatuses that display probe results by means of ultrasound with an image or a numerical value, such as a fish detector (sonar), and a defectoscope for non-destructive inspection.

As is obvious from the above description, the acoustic lens according to the present embodiment is an acoustic lens for an ultrasound probe, and is composed of a vulcanized molded rubber composition containing silicone rubber and metal oxide particles dispersed in the silicone rubber, in which the metal oxide particles have a number-average particle diameter of 30 to 2,000 nm, a specific gravity of 3.5 g/cm$^3$ or more, a content of 30 to 150 parts by mass based on 100 parts by mass of the silicone rubber, and an oil absorption amount of 20 mL or less per 100 g. Therefore, it is possible to provide an acoustic lens having excellent acoustic properties and being excellent in the mixing property between metal oxide particles and silicone rubber.

It is more effective for the metal oxide particles whose surface is basic, from the viewpoints of easy interaction between the silicone rubber having acidic properties and the metal oxide particles, and of further enhancing the mixing property between the metal oxide particles and the silicone rubber.

It is more effective for the vulcanized molded rubber composition to further contain aluminum oxide supported on the surface of the metal oxide particles, from the viewpoint of further enhancing the mixing property between the metal oxide particles and the silicone rubber.

It is more effective for the metal oxide particles to be titanium oxide particles or barium sulfate particles, from the viewpoint of further enhancing the mixing property between the metal oxide particles and the silicone rubber.

The method for producing the acoustic lens according to the present embodiment is a method for producing an acoustic lens for an ultrasound probe, the method including: producing a rubber composition by kneading silicone rubber with metal oxide particles; and vulcanizing and molding the rubber composition, in which the metal oxide particles having a number-average particle diameter of 30 to 2,000 nm, a specific gravity of 3.5 g/cm$^3$ or more, a content of 30 to 150 parts by mass based on 100 parts by mass of the silicone rubber, and an oil absorption amount of 20 mL or less per 100 g are used. Therefore, an acoustic lens produced according to the production method has excellent acoustic properties and is excellent in the mixing property between metal oxide particles and silicone rubber.

The ultrasound probe according to the present embodiment has the acoustic lens according to the present embodiment. Therefore, it is possible to stably provide an ultrasound probe having excellent acoustic properties.

The ultrasound imaging apparatus according to the present embodiment has the ultrasound probe according to the present embodiment. Therefore, it is possible to provide an ultrasound imaging apparatus capable of testing a test subject with high accuracy and reliability.

EXAMPLES

Hereinafter, the present invention will be described with reference to Examples. However, the present invention is not construed to be limited by these Examples.

In the present embodiment, sheets for evaluation were produced with the material for the acoustic lens to study the acoustic properties of the produced sheets.

1. Production of Sheet for Evaluation (Production of Sheet 1)

As metal oxide particles, rutile type titanium oxide particles A (TiO$_2$ A) having aluminum oxide being supported on the surface thereof were provided. Titanium oxide particles A have a number-average particle diameter of 40 nm, an oil absorption amount of 18 mL, and a specific gravity of 4.2 g/cm$^3$.

Titanium oxide particles A were laid thinly on a stainless pad, and allowed to stand for 4 hours in the environment of 140° C. Thus, moisture or the like attached to titanium oxide particles A was removed.

The following components in the following amounts:
Dimethylpolysiloxane 100 parts by mass
Titanium oxide particles A 40 parts by mass
were mixed and kneaded with a 6-inch double roll kneader to prepare a rubber composition.

As the silicone rubber, dimethylpolysiloxane in which both terminals of a molecular chain were substituted with a dimethylvinylsilyl group was used. The dimethylpolysiloxane is "KE742" manufactured by Shin-Etsu Chemical Co., Ltd. The viscosity of the silicone rubber is 5.3×10$^{-4}$ m$^2$/s, and the content of vinyl groups is 0.2 mol %.

0.5 part by mass of 2,5-dimethyl-2,5-di(t-butylperoxy)hexane as a vulcanizing agent was mixed into 100 parts by mass of the rubber composition. Then, the mixture was press-molded at 165° C. for 10 minutes, and subjected to secondary vulcanization at 200° C. for 2 hours to produce sheet 1 having a thickness of 2 mm.

(Production of Sheets 2 to 16)

Sheets 2 to 16 were produced in the same manner as sheet 1 except that, as metal oxide particles, rutile type titanium oxide particles B to F (TiO$_2$B to F), barium sulfate particles A to D (BaSO$_4$ A to D), zinc oxide particles A and B (ZnO A and B) or alumina particles (Al$_2$O$_3$) shown in Table 1 were respectively used, and that the contents of metal oxide particles were changed as shown in Table 1.

Titanium oxide particles B have a number-average particle diameter of 210 nm, an oil absorption amount of 15 mL, and a specific gravity of 4.2 g/cm$^3$.

Titanium oxide particles C have a number-average particle diameter of 210 nm, an oil absorption amount of 14 mL, and a specific gravity of 4.2 g/cm$^3$.

Barium sulfate particles A have a number-average particle diameter of 300 nm, an oil absorption amount of 16 mL, and a specific gravity of 4.5 g/cm$^3$.

Barium sulfate particles B have a number-average particle diameter of 280 nm, an oil absorption amount of 18 mL, and a specific gravity of 4.5 g/cm$^3$.

Barium sulfate particles C have a number-average particle diameter of 300 nm, an oil absorption amount of 18 mL, and a specific gravity of 4.5 g/cm$^3$.

Zinc oxide particles A have a number-average particle diameter of 35 nm, an oil absorption amount of 32 mL, and a specific gravity of 5.6 g/cm$^3$.

Zinc oxide particles B have a number-average particle diameter of 35 nm, an oil absorption amount of 38 mL, and a specific gravity of 5.6 g/cm$^3$.

Titanium oxide particles D have a number-average particle diameter of 35 nm, an oil absorption amount of 36 mL, and a specific gravity of 4.2 g/cm$^3$.

Titanium oxide particles E have a number-average particle diameter of 35 nm, an oil absorption amount of 34 mL, and a specific gravity of 4.2 g/cm$^3$.

Titanium oxide particles F have a number-average particle diameter of 200 nm, an oil absorption amount of 21 mL, and a specific gravity of 4.2 g/cm$^3$.

Barium sulfate particles D have a number-average particle diameter of 400 nm, an oil absorption amount of 23 mL, and a specific gravity of 4.5 g/cm$^3$.

Alumina particles have a number-average particle diameter of 140 nm, an oil absorption amount of 35 mL, and a specific gravity of 4.0 g/cm$^3$.

2. Evaluation (1) Evaluation of Failure Occurrence Rate

Failure occurrence rate at the time when producing 100 pieces of each of sheets 1 to 16 was evaluated. Failure occurrence was judged based on whether or not a streak-shaped defect with a length of 1 mm or more occurred. From the viewpoint of endurance in practical use, a case where the failure occurrence rate was five pieces or less was judged to be acceptable.

(2) Evaluation of Acoustic Properties

First, the density of each of sheets 1 to 16 was determined at 25° C. according to JIS. C-2123. Next, the sound velocity at 25° C. was measured for each of sheets 1 to 16 at a measuring frequency of 5 MHz using "Sing-around ultrasonic velocity measuring instrument UVM-2 (Ultrasonic Engineering Co., Ltd.)." Lastly, the product of the density and the sound velocity which were measured was used to determine the acoustic impedance of sheets 1 to 16. Generally, MRayl is used as a unit of acoustic impedance, and 1 MRayl means 1×10$^6$ kg/m$^2$s. From the viewpoint of endurance in practical use, a case where the acoustic impedance was 1.3 (MRayl) or more was judged to be acceptable.

(3) Evaluation of Attenuation Factor

When each of sheets 1 to 16 was immersed in a tank filled with water at a temperature of 25° C., 15 MHz ultrasound was generated in water using Ultrasonic Pulser Receiver JPR-10C (manufactured by Japan Probe Co., Ltd.) to measure amplitudes before and after the transmission of ultrasound through the sheet. From the viewpoint of endurance in practical use, a case where the attenuation factor was less than 8 (dB/mm) was judged to be acceptable.

Table 1 shows, for each of sheets 1 to 16, sheet No., type of metal oxide particles, number-average particle diameter, oil absorption amount, specific gravity, addition amount, type of support material, acoustic impedance, attenuation factor, failure occurrence rate (referred to simply as "occurrence rate" in Table 1), and category.

TABLE 1

| Sheet No. | Metal Oxide Particles | | | | Type of Support Material | Acoustic Impedance (MRayl) | Attenuation Factor (dB/mm) | Occurrence Rate (piece) | Category |
| | Type | Particle Diameter (nm) | Oil Absorption Amount (mL) | Specific Gravity (g/cm$^3$) | Addition Amount (parts by mass) | | | | | |
|---|---|---|---|---|---|---|---|---|---|---|
| 1 | TiO$_2$ A | 40 | 18 | 4.2 | 40 | Al$_2$O$_3$ | 1.30 | 7.00 | 2 | Ex. |
| 2 | TiO$_2$ B | 210 | 15 | 4.2 | 40 | — | 1.33 | 6.80 | 2 | |
| 3 | TiO$_2$ C | 210 | 14 | 4.2 | 40 | Al$_2$O$_3$ | 1.32 | 6.70 | 0 | |
| 4 | TiO$_2$ C | 210 | 14 | 4.2 | 50 | Al$_2$O$_3$ | 1.37 | 7.20 | 1 | |
| 5 | BaSO$_4$ A | 300 | 16 | 4.5 | 40 | — | 1.33 | 7.30 | 2 | |
| 6 | BaSO$_4$ B | 280 | 18 | 4.5 | 40 | Al$_2$O$_3$ | 1.33 | 6.60 | 0 | |
| 7 | BaSO$_4$ B | 280 | 18 | 4.5 | 50 | Al$_2$O$_3$ | 1.38 | 7.40 | 1 | |
| 8 | BaSO$_4$ C | 300 | 18 | 4.5 | 45 | SiO$_2$, Al$_2$O$_3$ | 1.32 | 7.30 | 2 | |
| 9 | ZnO A | 35 | 32 | 5.6 | 40 | — | 1.28 | 8.10 | 35 | Comp. Ex. |
| 10 | ZnO B | 35 | 38 | 5.6 | 40 | SiO$_2$ | 1.25 | 10.9 | 64 | |
| 11 | TiO$_2$ D | 35 | 36 | 4.2 | 40 | — | 1.28 | 10.2 | 43 | |
| 12 | TiO$_2$ D | 35 | 36 | 4.2 | 50 | — | — | — | — | |
| 13 | TiO$_2$ E | 35 | 34 | 4.2 | 40 | SiO$_2$ | 1.24 | 12.4 | 67 | |
| 14 | TiO$_2$ F | 200 | 21 | 4.2 | 40 | Al$_2$O$_3$ | 1.25 | 9.40 | 26 | |
| 15 | BaSO$_4$ D | 400 | 23 | 4.5 | 40 | — | 1.26 | 9.00 | 35 | |
| 16 | Al$_2$O$_3$ | 140 | 35 | 4.0 | 40 | — | 1.31 | 10.1 | 21 | |

In sheets 9 to 16 of comparative examples, metal oxide particles had an oil absorption amount of more than 20 mL. Accordingly, in sheet 9 to 11, and 13 to 16 of comparative examples, at least one of acoustic properties (acoustic impedance and attenuation factor) and failure occurrence rate was inferior. Further, in sheet 12 of comparative example, no acoustic lens could be molded, since there was a large amount of addition of metal oxide particles to silicone rubber. This is considered to be because the mixing property between the silicone rubber and the metal oxide particles was lowered due to the oil absorption amount of the metal oxide particles being more than 20 mL.

In contrast, in sheets 1 to 8 of examples, the metal oxide particles have a number-average particle diameter within a range of 30 to 2,000 nm, a specific gravity of 3.5 g/cm$^3$ or more, a content of 40 to 50 parts by mass based on 100 parts by mass of the silicone rubber, and an oil absorption amount of 20 mL or less per 100 g, and thus sheets 1 to 8 were excellent in acoustic properties (acoustic impedance and attenuation factor) with sufficiently low failure occurrence rate. In particular, as is obvious from sheets 4 and 7 of examples, even when there was a large amount of addition of the metal oxide particles to silicone rubber, it was possible to mold an acoustic lens at a low failure occurrence rate. This is considered to be because the mixing property between the silicone rubber and the metal oxide particles was increased.

INDUSTRIAL APPLICABILITY

According to the present invention, large amounts of metal oxide particles can be mixed into silicone rubber, and thus an acoustic lens having excellent acoustic properties can be stably produced in high yield. Therefore, according to the present invention, further spread of ultrasound probes and ultrasound imaging apparatuses is expected.

What is claimed is:

1. An acoustic lens for an ultrasound probe, the acoustic lens comprising a vulcanized molded rubber composition containing silicone rubber and metal oxide particles or barium sulfate particles dispersed in the silicone rubber, wherein
    a surface of the metal oxide particles or the barium sulfate particles is basic; and
    the metal oxide particles or the barium sulfate particles have:
    a number-average particle diameter of 30 to 2,000 nm;
    a specific gravity of 3.5 g/cm3 or more;
    a content of 30 to 150 parts by mass based on 100 parts by mass of the silicone rubber; and
    an oil absorption amount of 20 mL or less per 100 g.

2. The acoustic lens according to claim 1, wherein the vulcanized molded rubber composition further contains aluminum oxide supported on the surface of the metal oxide particles or the barium sulfate particles.

3. The acoustic lens according to claim 1, wherein the metal oxide particles are titanium oxide particles.

4. A method for producing an acoustic lens for an ultrasound probe, the method comprising:
    kneading silicone rubber with metal oxide particles or barium sulfate particles to produce a rubber composition; and
    vulcanizing and molding the rubber composition, wherein
    a surface of the metal oxide particles or the barium sulfate particles is basic; and
    metal oxide particles or barium sulfate particles having a number-average particle diameter of 30 to 2,000 nm, a specific gravity of 3.5 g/cm3 or more, a content of 30 to 150 parts by mass based on 100 parts by mass of the silicone rubber, and an oil absorption amount of 20 mL or less per 100 g are used as the metal oxide particles or the barium sulfate particles.

5. The method for producing an acoustic lens according to claim 4, wherein the metal oxide particles having aluminum oxide being supported on the surface thereof or the barium sulfate particles having aluminum oxide being supported on the surface thereof are used.

6. The method for producing an acoustic lens according to claim 4, wherein titanium oxide particles are used as the metal oxide particles.

7. An ultrasound probe comprising the acoustic lens according to claim 1.

8. An ultrasound imaging apparatus comprising the ultrasound probe according to claim 7.

9. An acoustic lens for an ultrasound probe, the acoustic lens comprising a vulcanized molded rubber composition containing silicone rubber and metal oxide particles, excepting aluminum oxide particles, or barium sulfate particles dispersed in the silicone rubber, wherein
    a surface of the metal oxide particles or the barium sulfate particles is basic; and
    the metal oxide particles or the barium sulfate particles have:
    a number-average particle diameter of 30 to 2,000 nm;
    a specific gravity of 3.5 g/cm3 or more;
    a content of 30 to 150 parts by mass based on 100 parts by mass of the silicone rubber; and
    an oil absorption amount of 20 mL or less per 100 g.

10. A method for producing an acoustic lens for an ultrasound probe, the method comprising:
    kneading silicone rubber with metal oxide particles, excepting aluminum oxide particles, or barium sulfate particles to produce a rubber composition; and
    vulcanizing and molding the rubber composition, wherein
    a surface of the metal oxide particles or the barium sulfate particles is basic; and
    metal oxide particles or barium sulfate particles having a number-average particle diameter of 30 to 2,000 nm, a specific gravity of 3.5 g/cm3 or more, a content of 30 to 150 parts by mass based on 100 parts by mass of the silicone rubber, and an oil absorption amount of 20 mL or less per 100 g are used as the metal oxide particles or the barium sulfate particles.

\* \* \* \* \*